US005459300A

United States Patent [19]

Kasman

[11] Patent Number: 5,459,300

[45] Date of Patent: Oct. 17, 1995

[54] MICROPLATE HEATER FOR PROVIDING UNIFORM HEATING REGARDLESS OF THE GEOMETRY OF THE MICROPLATES

[76] Inventor: David H. Kasman, 19 Ridge Rd., Holliston, Mass. 01746

[21] Appl. No.: 25,954

[22] Filed: Mar. 3, 1993

[51] Int. Cl.[6] ................ H05B 1/02; C12M 3/00

[52] U.S. Cl. ................ 219/433; 219/436; 219/459; 219/448; 219/456; 435/809

[58] Field of Search ................ 219/433, 456, 219/242, 521, 435, 436, 459, 385, 448; 435/293, 300, 301, 809

[56] References Cited

U.S. PATENT DOCUMENTS

| | | | |
|---|---|---|---|
| 4,116,777 | 9/1978 | Takatsy et al. | 195/127 |
| 4,666,853 | 5/1987 | Meserol et al. | 435/290 |
| 4,701,597 | 10/1987 | Braun et al. | 219/521 |
| 4,888,463 | 12/1989 | Middlebrook | 219/201 |
| 4,990,754 | 2/1991 | Bechevet et al. | 219/530 |
| 5,002,889 | 3/1991 | Klein | 422/102 |
| 5,274,215 | 12/1993 | Jackson | 219/439 |

OTHER PUBLICATIONS

Molecular Biology Products (Techne Princeton), Mar. 12, 1991.

DIGI-BLOCK Digital Block Heater (Laboratory Devices, Inc.) Sep. 1990.

EL 307 Manual Microplate Reader (Fisher Scientific) Jan., 1993.

*Primary Examiner*—Mark H. Paschall

*Attorney, Agent, or Firm*—Cesari and McKenna

[57] ABSTRACT

A heater which accommodates microwell plates having a variety of bottom and peripheral geometries. The heater consists of a thermally conductive compliant material layer disposed on a planar heated platen. The compliant layer is dimensioned such that it contacts the microplate along the bottoms of the wells only, and not along the peripheral portions thereof. A temperature sensor may be disposed within the compliant layer to provide an indication of the well temperature for accurate control.

18 Claims, 6 Drawing Sheets

MICROPLATE HEATER FOR PROVIDING UNIFORM HEATING REGARDLESS OF THE GEOMETRY OF THE MICROPLATES

FIELD OF THE INVENTION

This invention relates generally to laboratory instruments and particularly to a heater for a microwell plate which uniformly heats the microwells regardless of the geometry of the plate.

BACKGROUND OF THE INVENTION

Certain techniques in molecular biology, chemistry and other disciplines require the processing of many samples in precisely the same way. Such processing might be required, for example, as part of a screening process, a statistical analysis, or a large-scale assay project.

To expedite the processing of multiple samples simultaneously, various laboratory instrument manufacturers make available so-called microwell strips and microwell arrays. (collectively, "microplates"). Microplates are typically formed from a chemically inert plastic and provide a number of small wells for holding material or liquid samples.

Microplates are available in various configurations, for example, eight well, ninety six well, and 384 well arrays. Microwells are also available in strips, or rows, which may be assembled in groups to provide arrays. Microwell strips and plates of this type are manufactured and sold by a number of companies, including Fisher Scientific of Atlanta, Ga. The outer dimensions of microwell array plates are more or less standardized from manufacturer to manufacturer; however, the individual microwells, usually cylindrical in cross-section, are typically provided with different bottom geometries, including U-shaped, V-shaped, and flat.

Microplate arrays provide a convenient vehicle for processing a large number of samples in parallel. For example, these microplate supply companies sell multichannel pipetters specifically adapted for placing a precise amount of material in multiple wells at the same time. Indeed, specialized instruments are now available, such as a stepping chemical assay machine, which automatically process the samples in all of the wells of a microplate.

Often times, particular chemical processes require some sort of heating. The traditional methods to heat microplates to a desired temperature are floating them on water in a constant temperature bath, or placing them on a rack in a gravity or convection incubator. In each of these methods, the heat transfer medium, be it water or air., can be easily held at the desired temperature, and thus these might appear to be satisfactory methods.

Unfortunately, since the wells situated on the periphery of the microplate have more surface area in contact with the water or circulating air than the inner wells, the peripheral wells will heat faster than the inner wells. This phenomenon, known as an "edge effect", can cause errors in certain processes. In the case of diagnostic tests, for example, which can be very temperature sensitive, these edge effects may sometimes completely, mask test results.

Some manufacturers have developed products specifically targeted at heating microplates. For example, Techne, Inc., of Princeton, N.J., has resorted to manufacturing their own special thin-walled plates and precisely machined heater platens that exactly match the geometry of the plates. Techne's heaters do not permit the use of plates manufactured by other companies or with different well configurations, however.

Lab-Line Instruments, Inc. of Melrose Park, Ill., has introduced a heater consisting of a machined aluminum block having a rectangular milled pocket in which a microwell plate can be placed. Upon heating the block, the surrounding air is heated, which in turn heats the microplate. The air gap between the heated block and the microplate results in extremely slow heating of such that it may take tens of minutes for the microplate to thermally stabilize. Even then, the microplate may never reach a temperature approaching the temperature of the block. In addition, the outer peripheral microwells present a larger surface area to the heated air than the inner microwells, which results in uneven heating.

As previously mentioned, the microplates from different manufacturers typically do not have uniform geometries, apart from the size and spacing of the wells. For example, they may have U-shaped, V-shaped, or flat bottoms, and may also have peripheral frame members, flanges, interstitial webbing, or other geometric differences.

In addition, although known microplate heaters do typically have a feedback control circuit of some type to regulate the temperature of the heat source, no capability is provided for determining the temperature of the contents of the wells themselves. As a result, it is often difficult to determine the precise temperature to which the wells have been heated.

It thus has heretofore not been possible to design an apparatus which accurately and uniformly heats all of the wells in microplates of differing geometries quickly and at the same rate.

SUMMARY OF THE INVENTION

It is an object of this invention to provide a heater capable of quickly heating each of the wells in a microplate array at the same rate, regardless of the microplate's bottom and peripheral geometry. In addition, the heater should accurately control the temperature cycling by measuring the actual temperature of the samples in the wells as closely as possible, rather than the temperature of a heating element.

Briefly, a microplate heater in accordance with the invention consists of a thermal energy source, such as a heating platen, and thermal conduction means, contacting the heating platen, for transmitting thermal energy to the microplate. The thermal conduction means transmits thermal energy only to the bottom of each of the wells, and not to peripheral flanges or inter-well webbing, so that each of the wells is heated at substantially the same rate as the other wells.

In a preferred embodiment, the thermal conduction means is implemented as a layer of thermally conductive compliant material, such as a thermally conductive silicone rubber.

A temperature sensor is preferably disposed within the compliant layer, and connected to a conventional feedback control circuit, to provide precise measurement of well temperature, and hence precise regulation of the heating process.

The microplate may be held down against the thermal conduction means by a weighted cover plate. The cover plate may include an insulating material layer to prevent direct thermal conduction between the cover plate and the microplate. Alternatively, the cover plate may be fabricated as an open frame, which permits the operator to access the microwell array while the microplate is being heated.

There are many advantages to this arrangement. The primary heat transfer path is from the heating platen, through the thermal conduction means, to the bottoms of the wells. This insures that every well in the microplate is heated at the; same rate as the other wells, regardless of its position. This also insures that each well reaches the same temperature as the other wells.

Furthermore, the invention provides quick heating of the microwells, since they are placed in direct contact with the heat source. A microplate can be heated on the order of several degrees per minute.

The compliant thermally conductive layer permits the heater to accept many brands and styles of microplates having a wide variety of well bottom geometries.

Because the temperature sensor is placed within the compliant layer adjacent the well bottoms, a reasonably accurate indication of the actual well temperature is provided, rather than some other temperature, such as the heating element temperature. This is accomplished without the logistical problems of using a probe which would have to be placed within a well.

BRIEF DESCRIPTION OF THE DRAWINGS

The novel features believed to be characteristic of the invention are pointed out in the appended claims. The best mode for carrying out the invention and its particular features and advantages can be better understood by referring to the following detailed description, when read together with the accompanying drawings, in which:

DETAILED DESCRIPTION OF A PREFERRED EMBODIMENT

Figure 1:
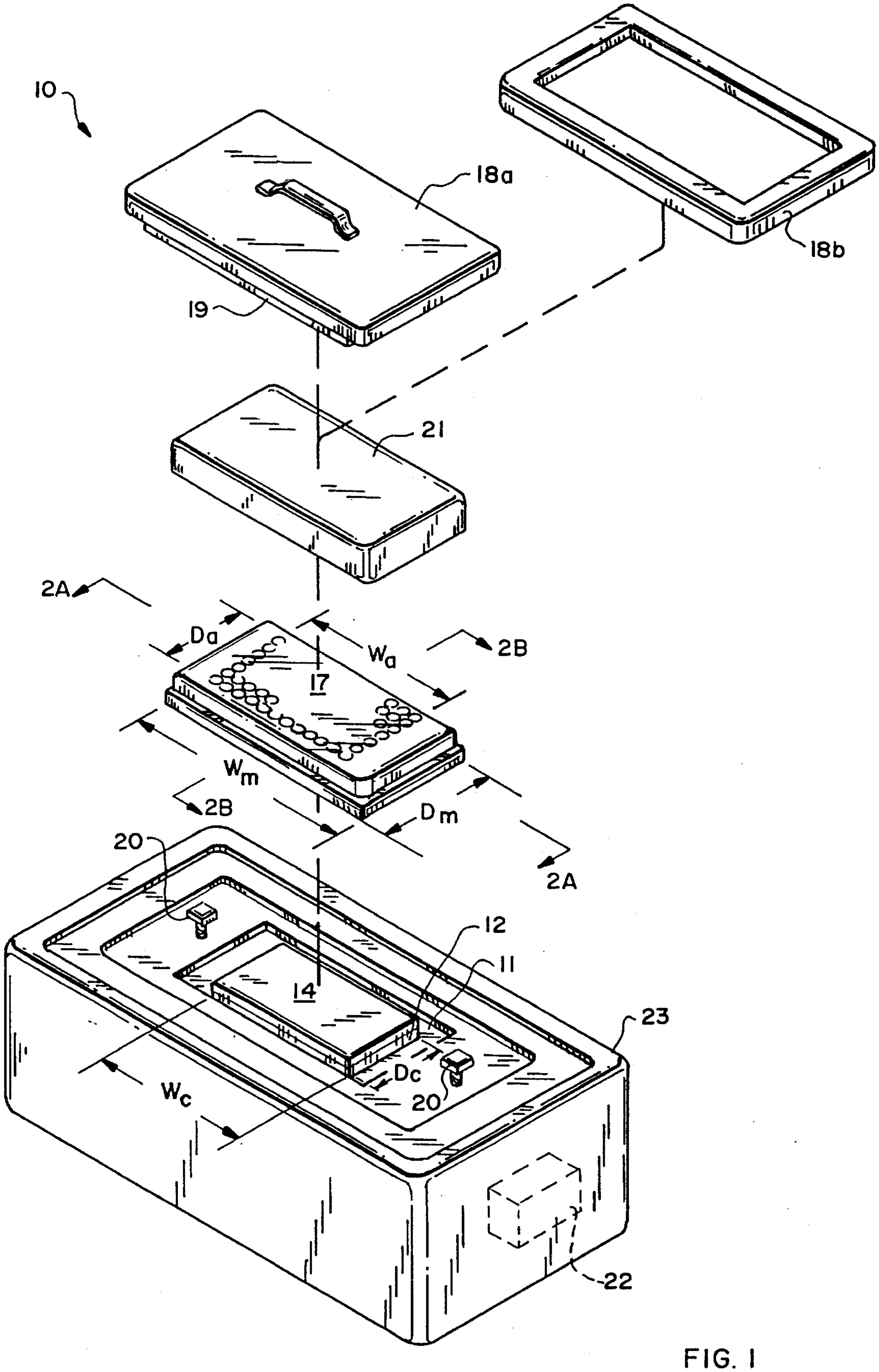
FIG. 1 is a three-dimensional view of a microplate heater according to the invention.

FIG. 1 shows a microplate heater 10 according to the invention. The heater 10 includes a base 11, a heating platen 12, and a thermal conduction means 14 situated on top of the platen 12. A microplate 16, containing a microwell array 17, is heated by positioning the microplate 16 over the thermal conduction means 14 when the platen 12 is energized. The preferred thermal conduction means 14 is formed as a layer of pliant material which permits transmission of heat.

Upon placing the microplate 16 within the heater 10, thermal energy passes from the heating element 12 through the compliant layer 14 to the bottoms of the wells in the microwell array 17. This insures that the surface area through which heat is transferred to each well is the same, regardless of the position of the well in the array 17.

A specifically formulated, thermally conductive silicone foam rubber is one possible material for the compliant layer 14: one particularly acceptable material is the so-called "COHRlastic" formulation number R-10404 sold by C, HR Industries of New Haven, Conn.

Other types of thermal conduction means 14 can also be used. For example, a flat, sealed, and flexible bag can be filled with a thermally conductive grease, oil gel, or even water. In addition, wools or fabrics formed of metal or other thermally conductive materials can be used.

The dimensions of the compliant layer 14 are chosen to insure even heating of microplates 16 along the bottoms 36 of the wells 32. For example, the compliant layer 14 preferably has a width $W_c$ and a depth $D_c$ smaller than the outer peripheral width $W_m$ and depth $D_m$ of the microplate 16. The width $W_c$ and depth $D_c$ of the compliant layer 14 are also slightly larger than the width $W_a$ and depth $D_a$ of the microwell array 17 contained in the microplate 16. This insures that the compliant layer 14 contain the microplate 16 only .along the well bottoms and not in other places.

A cover is preferably used to cause, the well array 17 to be pressed downward into the compliant layer 14. A rectangular weighted cover such as the illustrated cover **18*a* may be used. An open cover 18*b* may also be used instead, if the operator desires to access well array 17 while the microplate 16 is positioned in the heater 10. In addition, the cover 18*a* or 18*b* may include fasteners such as clamps or screws (not shown in FIG. 2A) to further assist in pressing the microplate 16 into the compliant layer 14**.

The cover **18*a* or 18*b* may also be fitted with a thermal insulator 19 to prevent the cover 18*a* or 18*b* from directly contacting the microplate 16. The insulator 19** is typically formed from a rigid foam plastic.

To assist in positioning the weighted covers **18*a* and 18*b*, the base 11 may be fitted with aligning guides 20. In that case, the guides 20 are designed to assist with aligning the cover 18*a* or 18*b* into position over the microplate 16**.

The heating platen 12 is typically formed as an aluminum plate. It may, for example, be an aluminum heating element sold by the Watlow Electric Manufacturing Company of St. Louis, Mo. under the trademark "Thincast". The temperature of the heating element 12 is controlled in a conventional fashion such as by a temperature control circuit 22.

The microplate 16 is usually formed of a thermally stable plastic, such as polystyrene or a thin polycarbonate.

A microplate cover 21 may be available for certain types of microplates 16, to keep the samples from being contaminated. In such an instance, the microplate cover 21 may remain on the microplate 16 during the heating process.

A housing 23 preferably used to support the base 11, heating platen 12, and compliant layer 14. The temperature control circuit 22 is also placed in the housing 23 to regulate the temperature of the heating platen 12 in a known, conventional fashion.

Figure 2A:
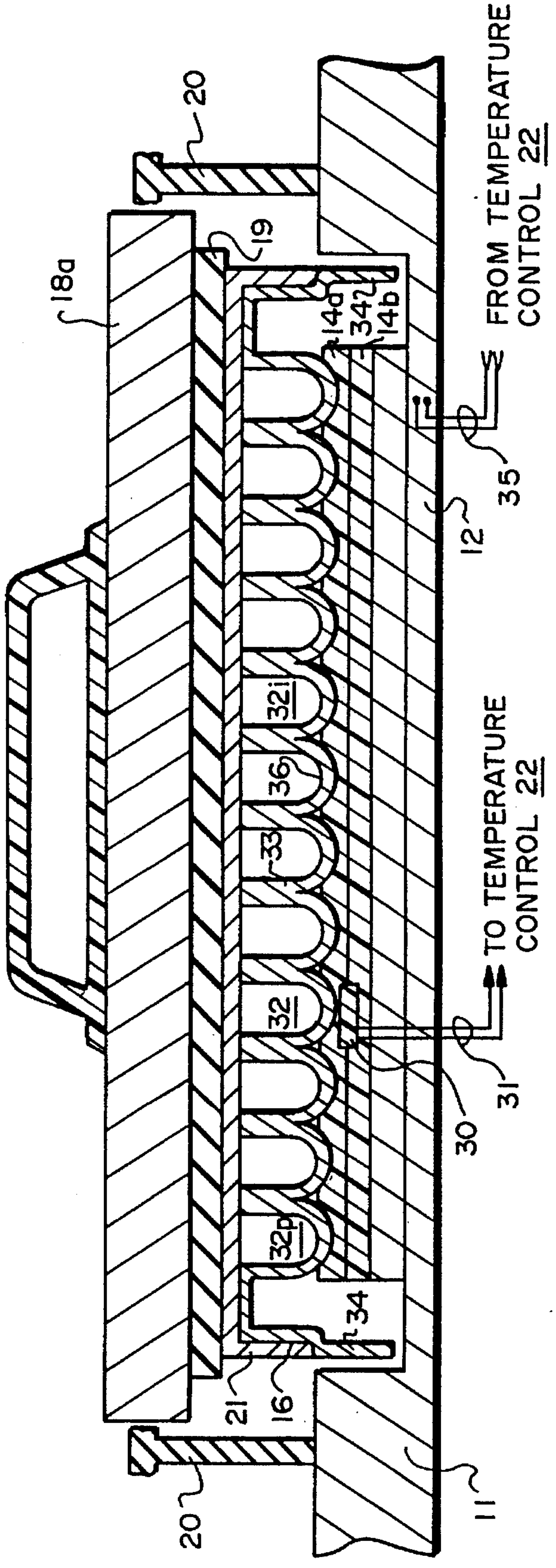
FIG. 2A is a cross-sectional view taken along lines 2A—2A of FIG. 1, showing a microplate installed in the heater, and the orientation of the thermally conductive compliant layer.

FIG. 2A is a cross-sectional view showing the heater 10, and in particular the microwell array 17 and its individual wells 32, in greater detail. The microplates 16 available from different manufacturers typically have wells 32 with different bottom geometries, including U-shaped, V-shaped, and flat-bottomed. In addition, the exact geometry of the periphery of the microplates 16 varies from different manufacturers, with some manufacturers providing them with outwardly extending peripheral flanges 34 and others with inwardly extending flanges 34 (such as that shown in FIG. 4).

As shown in FIG. 2A, when the weighted cover **18*a* is placed on the microplate 16, the bottoms 36 of the wells 32 press into the compliant layer 14. As soon as the microplate 16 is positioned in this way, heat is transferred to the bottom 36 of each well 32 from the heated compliant layer 14**.

During this process, the heating platen 12 has sufficient mass, and hence sufficient thermal inertia, to remain at nearly a constant temperature. The temperature of each well 32 thus soon stabilizes near the temperature of the compliant layer 14 which is also quickly brought to equilibrium with the platen 12. In practice, the wells 32 may be heated at a rate of several degrees per minute, a significant speed advantage over prior microplate heating methods.

Figure 4:
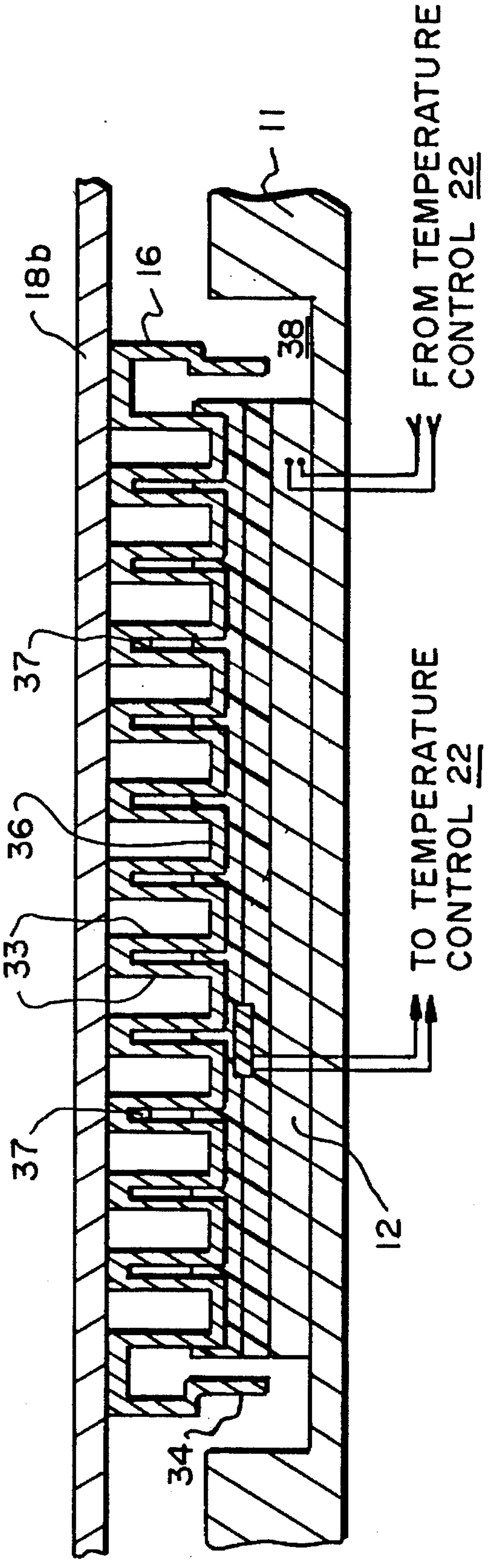
FIG. 4 is a cross-sectional view of the microplate heater and a microplate such as that shown in FIG. 3B.

Each well 32 contacts the compliant layer 14 only along its bottom portion 36, and no part of the compliant layer 14, heated platen 12, cover 18*a*, or any other potential thermal source contacts the well walls 33 or any inter-well webbing 37 (FIG. 4). As a result, virtually all heat is transmitted to the wells 32 via the compliant layer 14 to the bottoms 36 of the wells 32.

It is also ensured that a well 32*p* located at the periphery of the array 17 is heated at the same rate as a well 32*i* located in the interior of the array 17. This is because the surface area over which each well 32 contacts the thermal conduction means 14 is the same, regardless of the position of the well 32.

It is possible that the flange 34 may make minimal contact with the base 11 or otherwise become heated to some extent. However, since the thermal resistance between a peripheral microwell 32*p* and the flange 34 is quite a bit higher than the thermal resistance between the peripheral well 32*p* and the compliant layer 14, relatively little heat is transferred to the microwell 32*p* from the flange 34.

Also evident from FIG. 2A is the fact that the compliant layer 14 is preferably formed of two layers 14*a* and 14*b* of material. A thermal sensor 30 is disposed between the compliant layers 14*a* and 14*b*, adjacent one of the wells 32. A set of leads 31 are connected to the sensor 30, to provide an indication of the current temperature in the compliant layer 14 back to the temperature control electronics 22.

The sensor 30 is preferably positioned in this way because the temperature of greatest concern is the temperature of the wells 32 themselves, and not necessarily the temperature of the heated platen 12. By placing the sensor 30 between the layers 14*a* and 14*b*, adjacent the wells 32, a temperature closer to the actual temperature of the wells 32 is measured than if the sensor 30 were placed within the heating element 12, for example. This is accomplished without placing the sensor 30 within the wells 32 or otherwise interfering with insertion and removal of the microplate 16 from the heater 10, or other possible sample contamination.

Lead wires 35 provide electric current from the temperature control circuit 22 to energize the heating element 12.

Figure 2B:
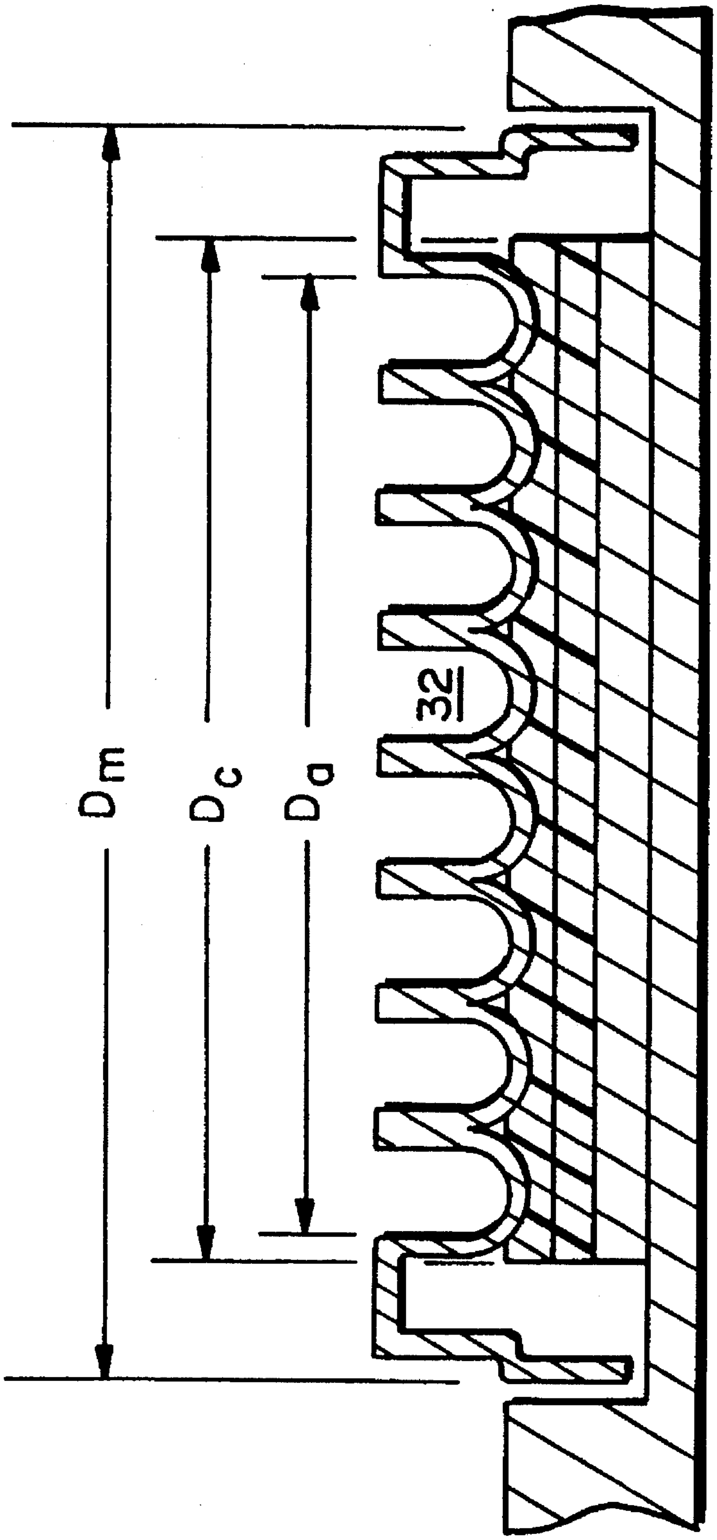
FIG. 2B is another cross-sectional view taken along lines 2B—2B of FIG. 1.

FIG. 2B is a partial cross-sectional view taken along line 2B—2B of FIG. 1. It illustrates that the depth $D_c$ of the compliant layer is less than the depth $D_m$ of the periphery of the microplate 16, but greater than the depth $D_a$ of the well array 17.

Figure 3A:
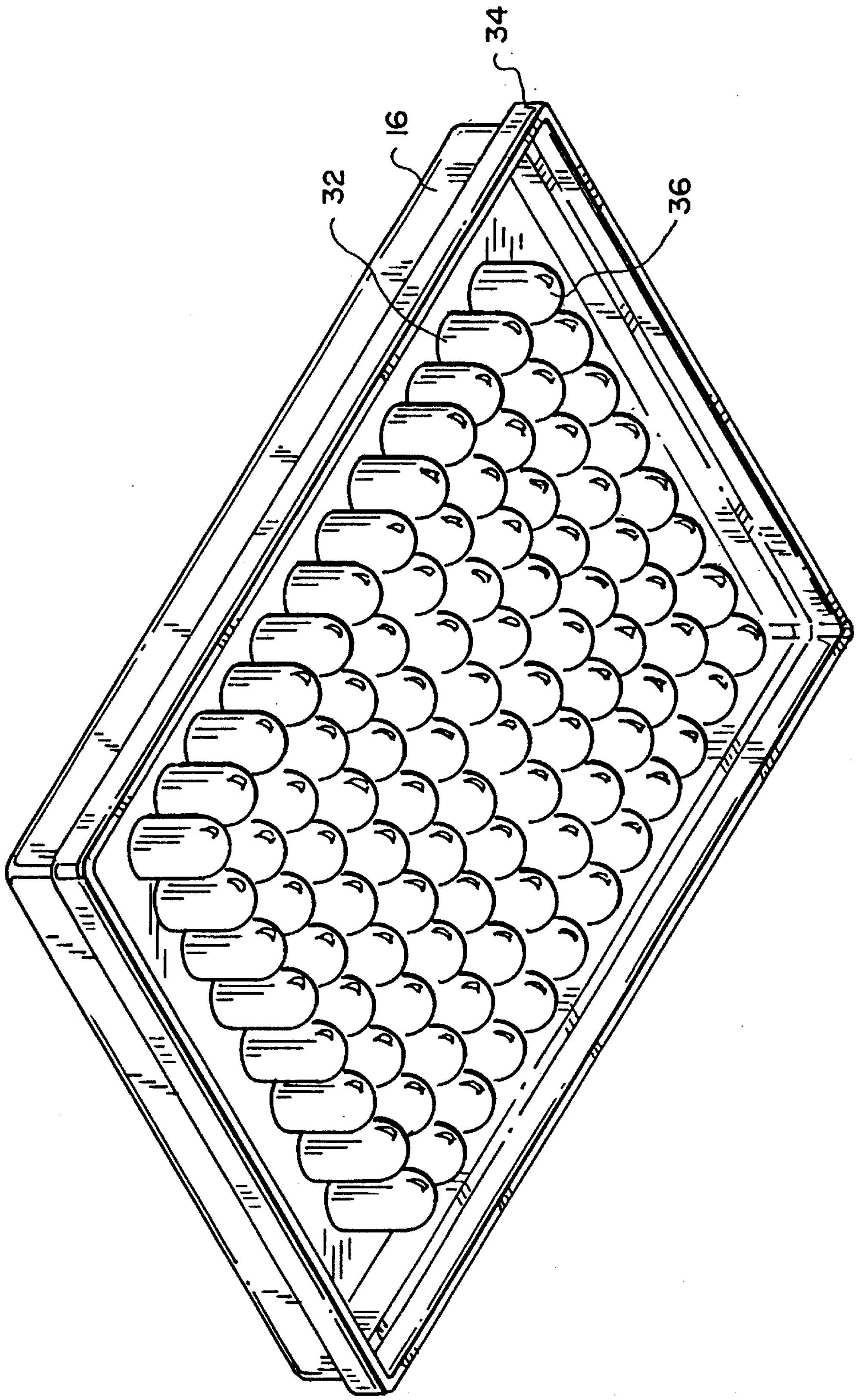
FIGS. 3A and 3B are isometric views of various microplates, showing examples of the different bottom geometries that are accommodated by the microplate heater.

FIG. 3A is a bottom isometric view of the microplate 16 shown in FIG. 2; the rounded well bottoms 36 are clearly visible, as is flange 34.

However, other microplates 16 have different geometries. For example, the microplate 16 shown in FIG. 3B has wells 32 with flat bottoms 36. In addition, the flange 34 of this microplate 16 extends inward from its periphery; that is, the lower dimension of the flange 34 is smaller than its upper dimension.

Figure 3B:
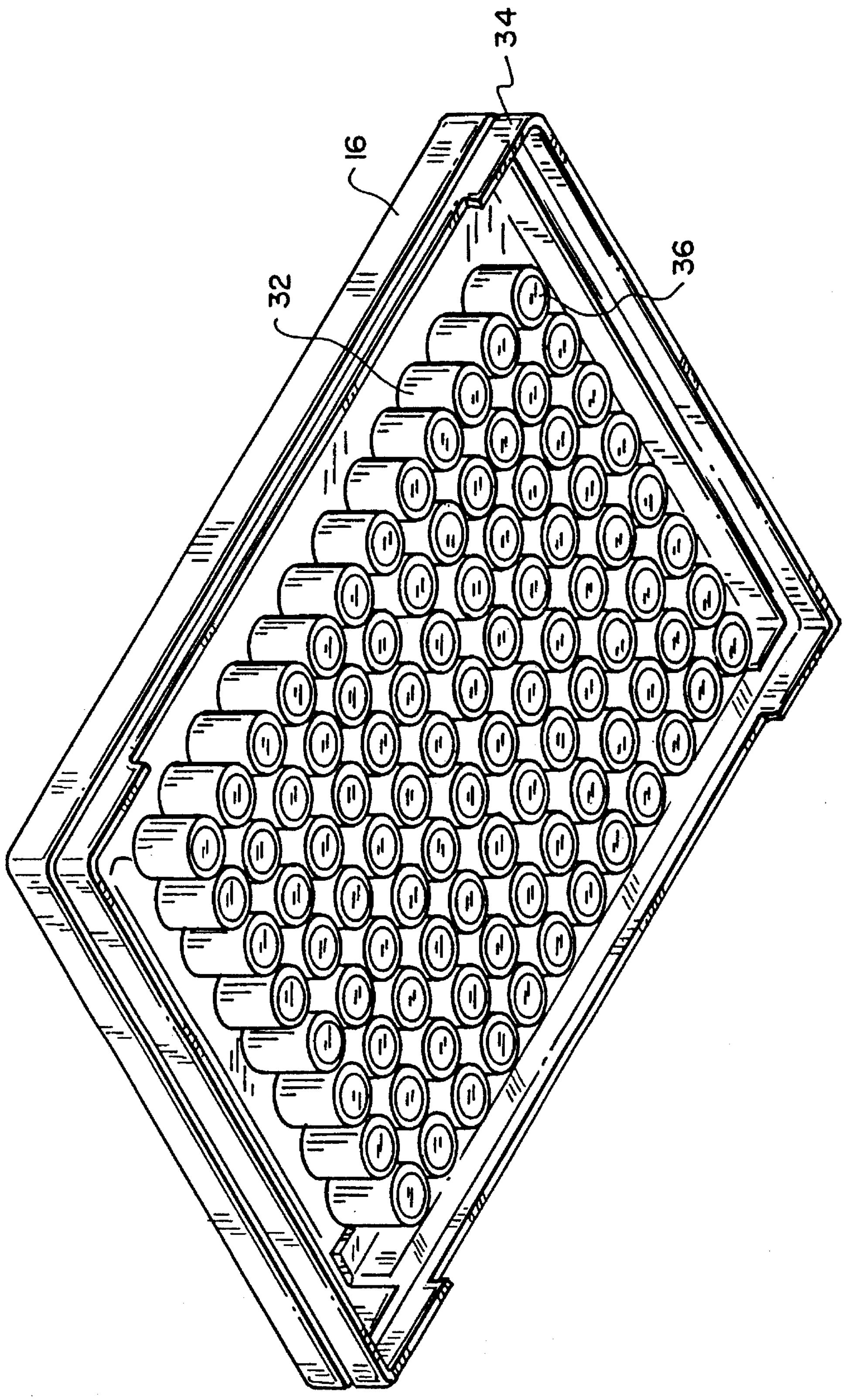

FIG. 4 is a cross-sectional view similar to that of FIG. 2, but showing the microplate 16 of FIG. 3B inserted into the heater 10. In this instance, the compliant layer 14 has conformed itself to the rectangular bottom geometry of the wells 32. In addition, the inwardly extending flanges 34 are accommodated in the splice 38 formed between the base 11 and the heating element 12.

Thus, despite the fact that the bottom and peripheral geometry of microplates 16 may differ from manufacturer to manufacturer, they can be accommodated by the same heater 10. Predictable results are obtained, regardless of the differences in bottom geometry, since each well 32 is heated only at its bottom 36, and not through its walls 33. As a result, the same amount of heat energy is applied to each of the wells 32.

An accurate indication of the temperature within the wells 32 (and thus accurate control of the heating process) is also accomplished, by having the temperature sensor 30 placed within the compliant layer 14 positioned adjacent the wells 32.

The terms and expressions which have been employed above are used as terms of description and not meant to be limiting in any way, and there is no intention to exclude any equivalents of the features shown and described or portions thereof, and it should be recognized that various modifications are possible while, remaining within the scope of the invention as claimed.

For example, other techniques can be used to insure that the wells 32 are heated on their bottom portions over a surface area which is the same regardless of the position of the wells 32, such as by using a support to float the microplate over the surface of a fluid bath at such an elevation that only the well bottoms 36 are immersed in the fluid.

In addition, although the invention has been described as using a heating platen 12, a source of cold thermal energy could also be used to chill a microplate in much the same manner. For example, a Pelletier thermoelectric heat pump can be used to heat or cool a metal platen 12.

What is claimed is:

1. A temperature control apparatus for controlling the temperature of a microplate containing a plurality of microwells, the apparatus comprising:

a thermal energy source; and means for transferring thermal energy from the thermal energy source to the microplate, said means being adaptable to engage microplates of varying shapes such that thermal energy is transferred substantially only to the bottom surfaces of the microwells and is transferred at substantially the same rate to microwells disposed in the interior of the microplate as it is transferred to microwells disposed on the periphery of the microplate.

2. An apparatus as in claim 1 wherein the thermal energy source is an aluminum heating platen.

3. An apparatus as in claim 1 wherein the means for transferring thermal energy comprises a thermally conductive compliant material layer.

4. An apparatus as in claim 3 wherein the compliant layer is formed of silicone foam rubber.

5. An apparatus as in claim 3 wherein the compliant layer comprises a fluid material disposed in a compliant container.

6. An apparatus as in claim 3 additionally comprising:

a cover, dimensioned to contract the upper periphery of the microplate, for pressing the microplate into the compliant layer.

7. An apparatus as in claim 6 wherein the cover is weighted.

8. An apparatus as in claim 6 wherein the cover additionally comprises a layer of insulating material, disposed on the bottom of the cover, to prevent conduction of thermal energy to the microplate from the cover.

9. An apparatus as in claim 3 wherein said layer is removable from said thermal energy source.

10. An apparatus as in claim 4 wherein said silicone foam rubber is loaded with a thermally conductive medium.

11. An apparatus for heating a microplate, the microplate containing an array of regularly spaced microwells, the apparatus comprising:

a heating platen having a planar surface; and a thermally conductive compliant and resilient layer, disposed on the planar surface of the heating platen, for adaptively receiving microplates whose bottom surfaces have varying geometries, said layer dimensioned such that heat from said platen is transferred substantially only to the bottoms of said microwells.

12. An apparatus as in claim 11 wherein the thermally conductive compliant layer consists of two individual material layers positioned adjacent one another.

13. An apparatus as in claim 12 additionally comprising:

a temperature sensor, disposed between the two individual material layers; and a temperature control circuit, connected between the temperature sensor and the heating platen, to regulate the heating platen temperature.

14. An apparatus as in claim 11 wherein the layer is formed of silicone foam rubber.

15. An apparatus as in claim 14 wherein said silicone foam rubber is loaded with a thermally conductive medium.

16. An apparatus as in claim 11 wherein the layer comprises a fluid material disposed in a compliant container.

17. A method of heating an array of wells for holding samples, the wells being formed in a microplate, the method comprising the steps of:

heating a compliant thermally conductive layer; and engaging the microplate with said compliant layer, such that only the bottoms of the wells physically contact said layer and heat is transferred at substantially the same rate to each of said well bottoms.

18. The method of claim 17 additionally comprising the step of:

measuring the temperature in the compliant layer adjacent one of the well bottoms.

* * * * *